(12) United States Patent
Su et al.

(10) Patent No.: US 7,621,636 B2
(45) Date of Patent: Nov. 24, 2009

(54) WORKING DISTANCE AND ALIGNMENT SENSOR FOR A FUNDUS CAMERA

(75) Inventors: Wei Su, Sunnyvale, CA (US); Yan Zhou, Pleasanton, CA (US); Qing Chun Zhao, Sunnyvale, CA (US); Yeou-Yen Cheng, Saratoga, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 146 days.

(21) Appl. No.: 11/621,943

(22) Filed: Jan. 10, 2007

(65) Prior Publication Data

US 2008/0165322 A1    Jul. 10, 2008

(51) Int. Cl.
*A61B 3/14* (2006.01)
*A61B 3/10* (2006.01)

(52) U.S. Cl. ...................... 351/206; 351/221
(58) Field of Classification Search ................ 351/200, 351/205–207, 210, 213–214, 221
See application file for complete search history.

(56) References Cited

U.S. PATENT DOCUMENTS

| | | | |
|---|---|---|---|
| 4,436,389 A | 3/1984 | Sano | |
| 4,544,246 A * | 10/1985 | Crane et al. | 351/211 |
| 5,757,461 A * | 5/1998 | Kasahara et al. | 351/206 |
| 6,220,706 B1 | 4/2001 | Foley | |
| 6,247,813 B1 * | 6/2001 | Kim et al. | 351/206 |
| 6,361,167 B1 | 3/2002 | Su | |
| 2005/0286018 A1* | 12/2005 | Yamaguchi et al. | 351/205 |
| 2006/0268230 A1* | 11/2006 | Kogawa et al. | 351/206 |

* cited by examiner

*Primary Examiner*—Scott J Sugarman
*Assistant Examiner*—Dawayne A Pinkney
(74) *Attorney, Agent, or Firm*—Charles E. Krueger

(57) ABSTRACT

In embodiments of optical arrangements of a working distance sensor in a fundus camera that can improve the determination of a correct working distance as well as the transverse positioning of the camera a number of near infrared light sources are arranged to project a number of near infrared illumination beams into the visible light illumination path of the fundus camera and a live view of the retina under near infrared illumination is captured and displayed on a monitor. These embodiments of optical arrangements and associated methods will enable an operator to directly determine if there is any undesirable flare or other artifact appearing within a designated region on the infrared retina view as a result of a wrong alignment of the fundus camera with respect to the eye in terms of not only the working distance but also the horizontal and vertical positions. Pattern recognition algorithms can be used to further enhance the positioning sensitivity of the working distance sensor. An additional iris alignment sensor can be added to achieve a coarse alignment and also function as a measure to determine if the dilation of the iris size is sufficient for different mode of fundus imaging.

34 Claims, 14 Drawing Sheets

WORKING DISTANCE AND ALIGNMENT SENSOR FOR A FUNDUS CAMERA

TECHNICAL FIELD

One or more embodiments relate to a fundus camera for retina imaging. In particular, they relate to a fundus camera with a working distance detecting means so that the captured retina image is free from undesirable flair, artifact or ghost images.

BACKGROUND OF THE INVENTION

When imaging the retina (or fundus, these terms will be used interchangeably) of an eye, some of the illumination light beam from a light source may be reflected and/or scattered from the cornea, the iris and the crystalline lens of the eye. It is possible that this undesired reflected and/or scattered light resulting from the interaction of the illumination light beam with the anterior segment of the eye can be mixed with the imaging beam which comprises desired light reflected/scattered from the retina of the eye for photographic imaging or observational purposes. This undesirable mixing can result in the appearance of flair light, artifact, haze or ghost images on the retina image.

To get rid of these undesirable effects, an annular ring-shaped illumination light with a selected annular width and a numerical aperture can be focused at the cornea region to illuminate a large area of the retina, and the imaging path can be designed to occupy a space inside of the annular ring on the cornea. When the eye is properly positioned the illumination path has no overlap with the imaging path at the cornea, iris and crystalline lens so that light from the illumination beam will not be reflected and/or scattered into the imaging beam. However, to ensure that there is no undesirable effect on the retina image, a correct working distance between the objective lens of the fundus camera and the patient's eye must be maintained.

Typically, the maintenance of the working distance is accomplished by providing one (or more) light emitting element(s) (usually of the near infrared spectral range) behind a first lens at one side of the optical axis of an objective lens of the fundus camera and one (or more) corresponding light detecting element(s) behind a second lens at the other side of the optical axis. The light from the light emitting element is either focused or collimated by the first lens and directed to intersect the optical axis of the objective lens at a predetermined point and the light as reflected at the corneal surface is focused at the light sensing element by the second lens (see for example U.S. Pat. No. 4,436,389, U.S. Pat. No. 6,220,706). When the light sensing element receives a maximum signal, the working distance is considered correct.

A major problem associated with this approach is that the working distance determined by the approach is not always correct and is highly dependent on the surface profile and orientation of the cornea surface at the light intersection point. In other words, this approach will only work if the cornea surface that intersects with the light beam for working distance detection is not tilted with respect to the optical axis of the objective lens of the fundus camera. Unfortunately, this is not always the case. For example, when a doctor wants to image the peripheral region of the retina, he or she needs to orient the fundus camera at an angle with respect to the optical axis of the eye, and in such a case, the required correct working distance will in fact be slightly different from that for the central or non-peripheral retina imaging case. Meanwhile, the cornea region that intersects with the light beam for working distance detection will generally not be the apex with a normal that is coaxial with the axis of the objective lens. As a result, the distance thus determined by such an approach will be wrong. Similarly, if the cornea surface profile of the patient eye is not ideal, such as for those who have keratoconus or have had LASIK surgery, a wrong working distance will also be established using this prior art approach. The consequence is a retina image that will have undesirable flair or another artifact.

DETAILED DESCRIPTION OF EXAMPLE EMBODIMENTS

Overview

Figure 1:
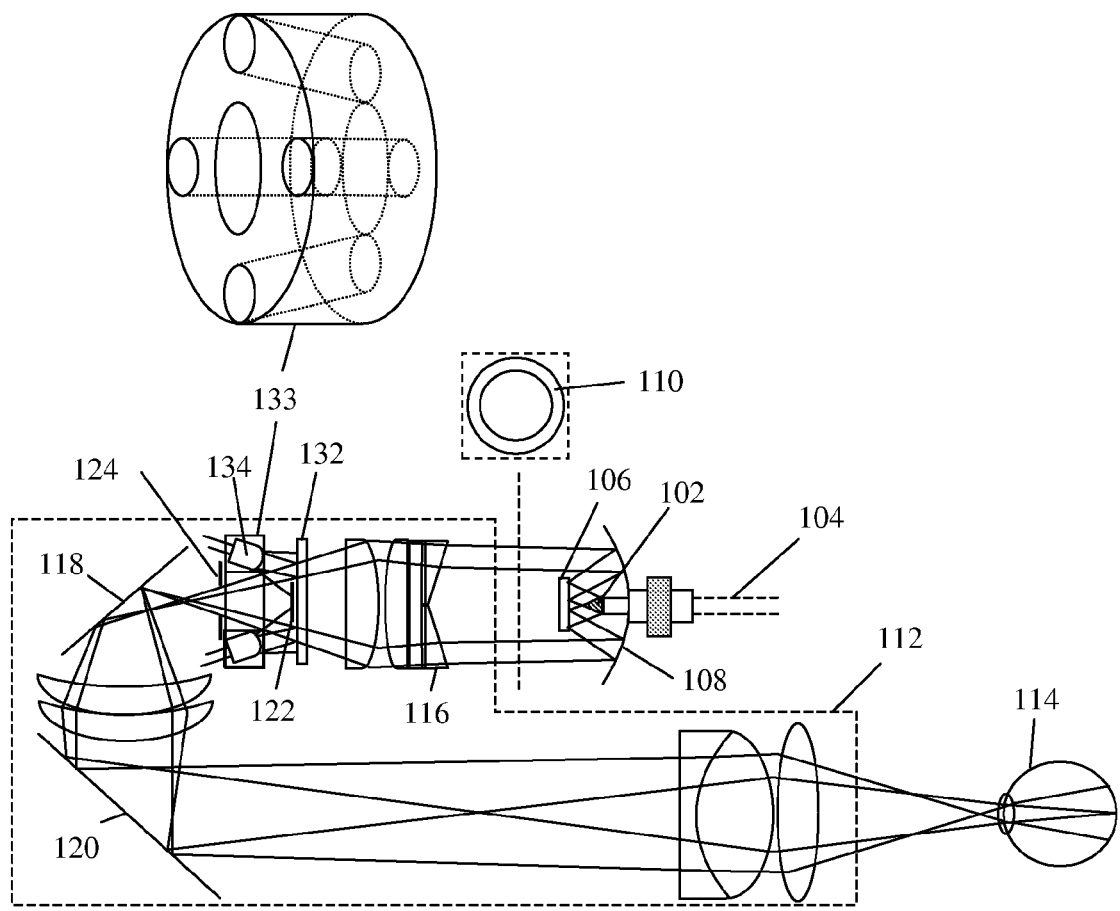
FIG. 1 shows one embodiment, in which near infrared light sources are arranged to project near infrared beams into the visible ring illumination path.

Various embodiments of the invention will be described where one embodiment is an optical arrangement of a working distance sensor in a fundus camera (note that the word fundus and retina are used interchangeably), and the associated method, in which one or more near infrared light sources such as a number of LEDs (light emitting diodes) are arranged to project a number of near infrared illumination beams into the visible light illumination path of the fundus camera. The near infrared beams may or may not substantially overlap with the visible illumination beam.

Due to the fact that the iris will generally not constrict when illuminated by near infrared light, a live view of the retina under near infrared illumination can be captured by a near infrared image sensor and displayed on a monitor before a visible retina image is taken. This live near infrared retina image can serve two purposes. Firstly, it will enable the operator to have a live view of the retina under near infrared illumination which preferably shows the same region as will be photographed with visible light. Therefore, the operator can identify the area of interest and make adjustments for the area to be photographed. Secondly, because the near infrared beams follow substantially the same path as the illumination beam of visible light, viewing the near infrared retina image will enable the operator to directly find out if there is any undesirable flair or any other artifact appearing within a designated region on the near infrared retina view as a result of wrong positioning of the fundus camera with respect to the eye in terms of not only the axial working distance but also the horizontal and vertical positions.

In one embodiment, this designated region on the near infrared live image can be selected to correspond to a clear visible image without flair or other artifact by correcting for any intended or unintended overlap or non-overlap of the near infrared illumination beam with the visible illumination beam and by correcting for any dispersion-induced-difference in the working distance resulting from the difference in the operating wavelength of the visible and the near infrared spectrum.

Viewing the near infrared image to determine correct working distance and alignment will always work regardless of the camera angle and the cornea surface profile. Therefore, a proper working distance can be maintained between the patient's eye and the camera under different viewing and photographing conditions.

In addition, in another embodiment, either image spots position sensing, pattern recognition, or a combination of both can be applied to the near infrared live image to provide a better indication of whether the fundus camera is positioned properly or not. This approach can ensure that there will be a minimum of or no annoying flair or other artifact appearing on the visible retina image to be captured.

DETAILED DESCRIPTION

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention.

FIG. 1 shows one embodiment of the illumination path. A beam of visible illumination light from a fiber bundle 104 is directed to a solid optically transparent cone 102 that is optically bonded to the output end of the fiber optic bundle 104. The cone 102 refracts the light rays from the fiber optic bundle 104 and, when combined with some other optical elements, transforms the visible illumination light rays into a ring beam. A mirror 106 can be arranged next to the cone tip to reflect the ring shaped radial-outwardly-deflected beam to a paraboloidal reflection mirror 108, which can collimate the ring beam. Various optical beam manipulation and/or relay configurations can be used to further spatially filter the ring beam and focus it into an annular ring of a desired size and numerical aperture at the cornea such that it can illuminate a desired area of the retina as has been described in a co-pending US patent application by Wei Su et al. entitled "Apparatus And Method For Delivering A Short Arc Lamp Light For Eye Imaging" filed Oct. 30, 2006 (U.S. patent application Ser. No. 11/606,597).

In this embodiment, one or more near infrared light source(s) 134, such as four non-coherent LEDs with a center wavelength at about 830 nm or four optical fibers with similar guided near infrared beams, can be used as the light sources. The near infrared light sources are positioned to project a corresponding number of near infrared beams into the visible ring illumination path. To achieve this, a dichroic mirror 132 that will transmit visible light but reflect near infrared light can be placed in the ring illumination path where the visible ring beam is radially converging.

In this embodiment, the near infrared light sources 134 can be mounted on a ring like structure 133 with an equal azimuthal angular separation of about 90 degrees, i.e. at the horizontal and vertical positions relative to the illumination path, and the axis of the LED-mounting ring structure 133 can be arranged to coincide with the optical axis of the illumination path. Four mounting holes for the LEDs on the ring structure 133 are tilted towards the central axis so that when the LEDs are mounted in the holes, near infrared beams can be aimed in a convergent manner toward the dichroic mirror 132, which will reflect the near infrared beams into the visible ring illumination path. The bigger center hole formed by aperture 124, which is located along the optical path of the ring structure, allows both the reflected convergent near infrared beam and the visible illumination beam to pass through. In general, the beams from the near infrared sources 134 should have a larger-than-needed beam width and numerical aperture and if the original numerical aperture of the near infrared LEDs is not large enough, a diffuser can be placed in front of each LED.

As one option, these near infrared beams can be introduced before the effective size and numerical aperture limiting stops of the ring illumination path. As illustrated in FIG. 1, after the near infrared beams are introduced into the illumination path, a first obscuration disk 122 can be used to limit the inner dimension of the annular illumination ring and a second circular aperture 124, which is coaxial with the obscuration disk 122, to form an annular ring, can be used to limit the outer dimension of the annular illumination ring. As a result, the spatially filtered near infrared beams will have a substantially overlapped path with the visible illumination beam path and will hence be relayed by the optics of the illumination path to the patient's eye in exactly the same manner as the visible illumination ring beam.

Note that the center wavelength of the near infrared light sources does not need to be limited to 830 nm, however it is an advantage to select a wavelength that will make visible in the near infrared image the major features of the patient's fundus, including the optical disk and the major blood vessels.

There are a number of alternative ways to introduce the near infrared beams into the illumination path. For example, the near infrared beams can be introduced at a location where the visible illumination ring is radially diverging, in which case the near infrared beams can also be aimed radially divergently at a dichroic beam combiner. Also the dichroic beam combiner can be one that reflects visible light and transmits near infrared light. In such a case, the near infrared beams can be introduced from behind a dichroic mirror at a location where the visible illumination ring beam is reflected and folded.

Figure 2:
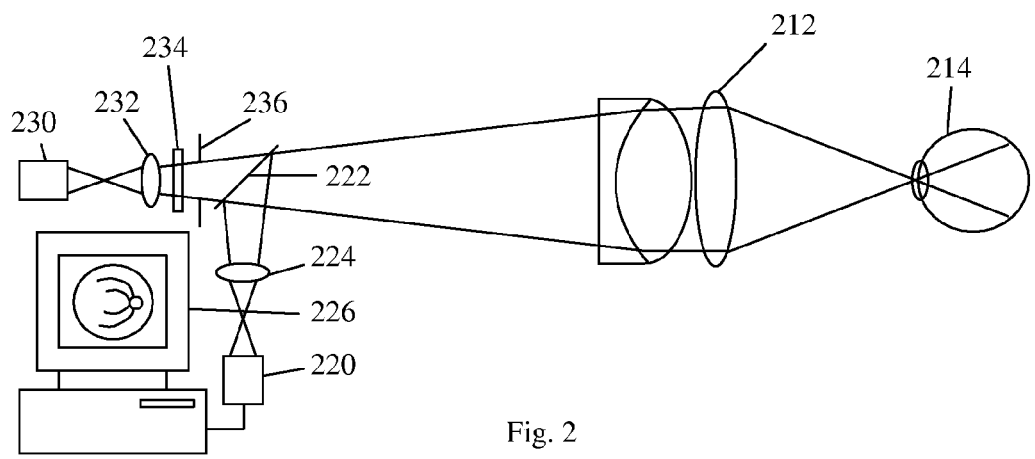
FIG. 2 shows one embodiment of the retina imaging path along with at least a portion of the near infrared retina imaging beam being tapped to form an image of the retina onto a near infrared CCD.

FIG. 2 shows one embodiment of the retina imaging path in which some optical elements such as the objective lens 212 that are used in directing the illumination beams to the eye 214 are shared and also used in the retina imaging optical path. As known in the art, optical elements for visible light can be shared with near infrared beams. However, the difference of the index of refraction for different wavelengths may require compensation as described below.

In one embodiment, at least a portion of the near infrared retina image formation beam is tapped, for example, using a beam splitter 222 somewhere along the retina imaging path and directed to an image sensor such as a near infrared CCD 220 (charge coupled device) to generate a live near infrared retina image which can also function as a working distance sensor. The imaging lens(es) 224 can be arranged to form and/or relay the near infrared image onto the near infrared CCD camera 220. The formed image can be relayed once or a number of times as long as it is substantially conjugate to the retina image planes of the retina imaging path.

In one embodiment, the effective aperture of the near infrared image relay system is of the same size as that of the visible light retina imaging path and is optically conjugated with it, so that the near infrared field of view is substantially the same as the field of view of the visible light. In practice, the images (and artifacts if any) observed under near infrared illumination are of exactly the same fashion and form as in the cases where visible light illumination is used. Since the eye is circularly symmetric, the effective apertures of illumination and the retina imaging paths are also preferably circular and as a result, both the near infrared and the visible retina images will be circular. The CCD 220 is preferably black and white with high near infrared sensitivity so that weak near infrared light returned from the retina can be detected. Because the sensing area of most CCDs is not square but rectangular, in this embodiment the field of view for the live near infrared image is designed such that the peripheral of the objective lens fits inside the shorter dimension of the image frame. The captured live near infrared image can be displayed on any type of monitor 226. For example, the image can be displayed on an LCD screen mounted on the fundus camera body.

The tapping of the near infrared image formation beam can be achieved in various ways. Although a partial reflection beam splitter 222 can be arranged in the imaging path to reflect a small portion of the near infrared beam as shown in FIG. 2, the beam splitter can also be a dichroic mirror to allow the reflection of the near infrared light and the transmission of visible light, in which case the reflected near infrared beam can be directed to a near infrared CCD 220 and the transmitted visible retina imaging beam can be directed to form a visible retina image on a color CCD 230 through a lens 232. A visible band pass optical filter 234 can be arranged before the color CCD 230 but after the beam splitter or dichroic mirror 222 to remove any remaining near infrared red light from entering the color CCD 230.

As another example, a polarization beam splitter can be mounted in the retina imaging path, for example near the system aperture 236, to separate a portion of the returning near infrared beam for working distance sensing. It is well known to those skilled in the art that retina scattered light will be depolarized while specularly reflected light from the cornea surface will not. Therefore, the method of using a cross polarization arrangement to reduce specular reflection from the cornea can be applied to the near infrared light as well as for the visible light. For example, a broad band first polarizer can be arranged in the illumination path and a second cross polarizer can be arranged in the imaging path to substantially reduce cornea specular reflection from getting into the retina imaging sensor(s).

Note also that the near infrared and the visible retina imaging paths can also be combined into one beam instead of being separated into two beams. In this case, the same imaging sensor can be used both for receiving a live near infrared retina image and for capturing a visible color retina image. Additionally, the near infrared light sources and the visible illumination light source can be turned on/off sequentially so that when a live near infrared retina image is to be observed, only the near infrared LEDs are turned on and when a color image of the retina is to be taken, the near infrared LEDs will be turned off before a pulse of the visible light, typically from a Xenon arc lamp, is flashed.

In one embodiment, the live near infrared retina image is used as a working distance sensor. In another embodiment, the same live image can also be used as an indication for transverse positioning. Although the infrared illumination light source can be in the form of a ring as in the case of the visible illumination light, in one embodiment a number of, for example four, near infrared LEDs or four fiber guided sources are used as the near infrared light sources. With this arrangement, four focused near infrared beams will be formed at the cornea region of the patient's eye, in exactly the same fashion as the visible illumination light ring beam will be focused into a narrow annular ring there. These four focused beams will be scattered and/or reflected by the media at the anterior portion of the eye, including the cornea, the iris, and the crystalline lens. The multiple infrared beams are distributed evenly along a circle, which is centered at the imaging optical axis. As seen in the monitor, the locations and symmetric nature of the four (or multiple) infrared bright spots could provide a clear indication for the transverse position alignment.

If the effective aperture of the near infrared retina image relay system is of the same size as that of the visible retina imaging path and is virtually coincident with it, and if the eye is well positioned transversely and also axially at the correct working distance, then the scattered near infrared light will always exist outside the retina imaging path and hence will not be captured by the working distance sensor.

Figure 3A:
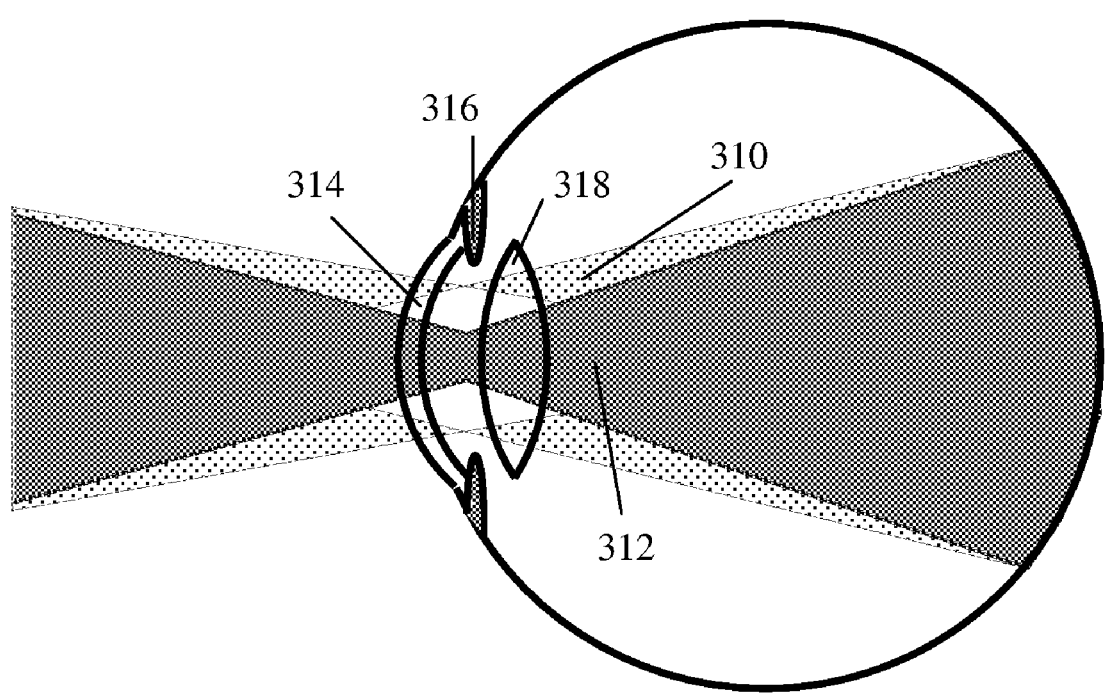
FIG. 3(a) shows an example of the space occupied respectively by the illumination path and the retina imaging path. When the eye is well positioned, there is no overlap of the illumination path with the imaging path at the cornea, the iris and the crystalline lens. Therefore, illumination light scattered by these tissues will not get into the imaging path.

FIG. 3(a) shows the illumination beam 310 and the retina image formation beam 312. Note that at the region of the anterior segment of the eye, when the eye is well positioned, there is no overlap of the illumination beam 310 with the imaging beam 312 at the cornea 314, the iris 316 and the crystalline lens 318. Therefore, scattered light of the illumination beam by the cornea 314, the iris 316 and the crystalline lens 318 will all propagate outside the light capturing zone of the imaging path and hence will not be relayed to the imaging sensor(s). In such a case, the working distance sensor will display a near infrared image of the retina without any flair or other artifact.

Figure 3B:
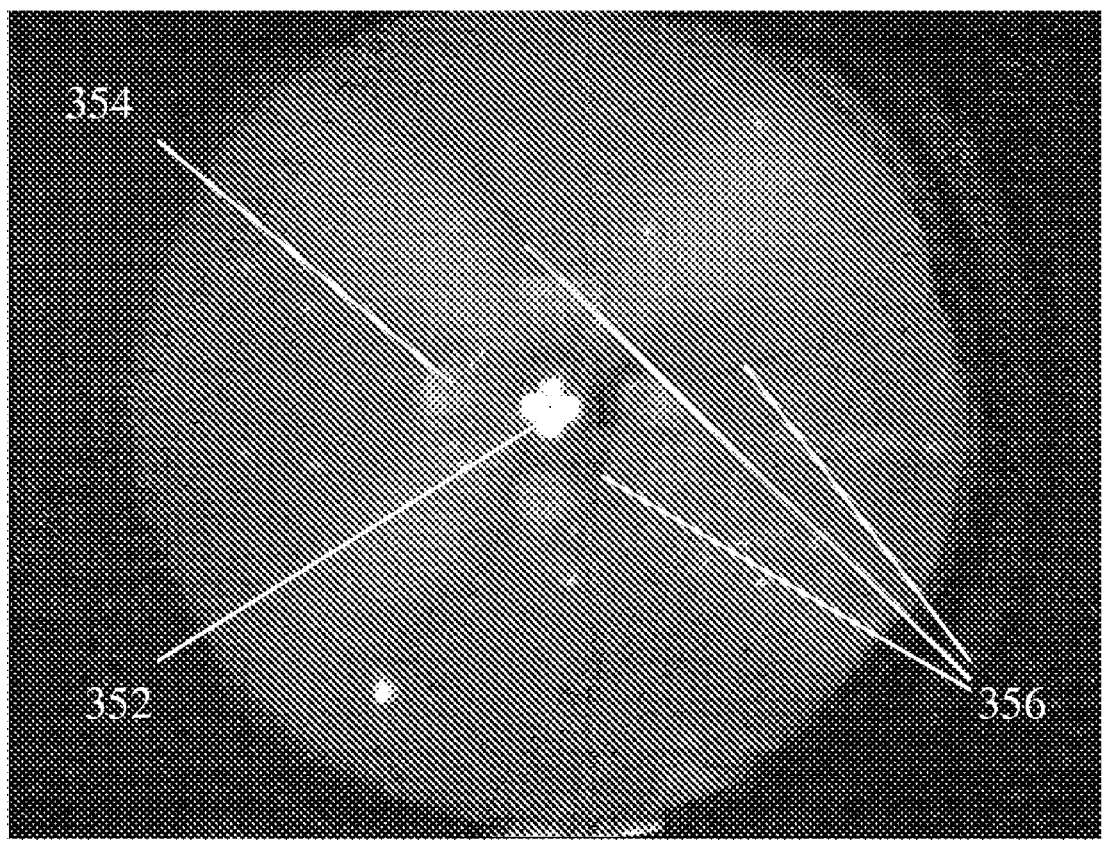
FIG. 3(b) shows a typical example of a near infrared retina image of the working distance sensor for the case of FIG. 3(a) when there is no flair.

FIG. 3(b) shows an example of such an image. It can be seen that within the image field, especially in the outer peripheral region, there are no spots, artifacts, or flare. This means that when a visible retina image is taken, there will not be any flare or artifact as well. Note that the central white cross pattern 352 and the four weaker spots 354 are caused by optical interface reflection from the objective lens. These patterns will be substantially suppressed in the visible retina image as a result of the visible high extinction ratio of crossed polarizers used. The three dark lines 356 are intentionally made on the retina surface of the fake eye to be used to represent major blood vessels.

If the working distance is not right, the illumination zone (for both near infrared and visible light) could be overlapped with the imaging path at the anterior region. As a result, the scattered and/or reflected light from the anterior portion of the eye can leak into the retina imaging path and appear as flair or other type of artifact on the working distance sensor. In other words, if a flair or other type of artifact is going to appear in the color retina image, the same effect from the near infrared LEDs will also be seen by the near infrared working distance sensor camera.

Figure 4A:
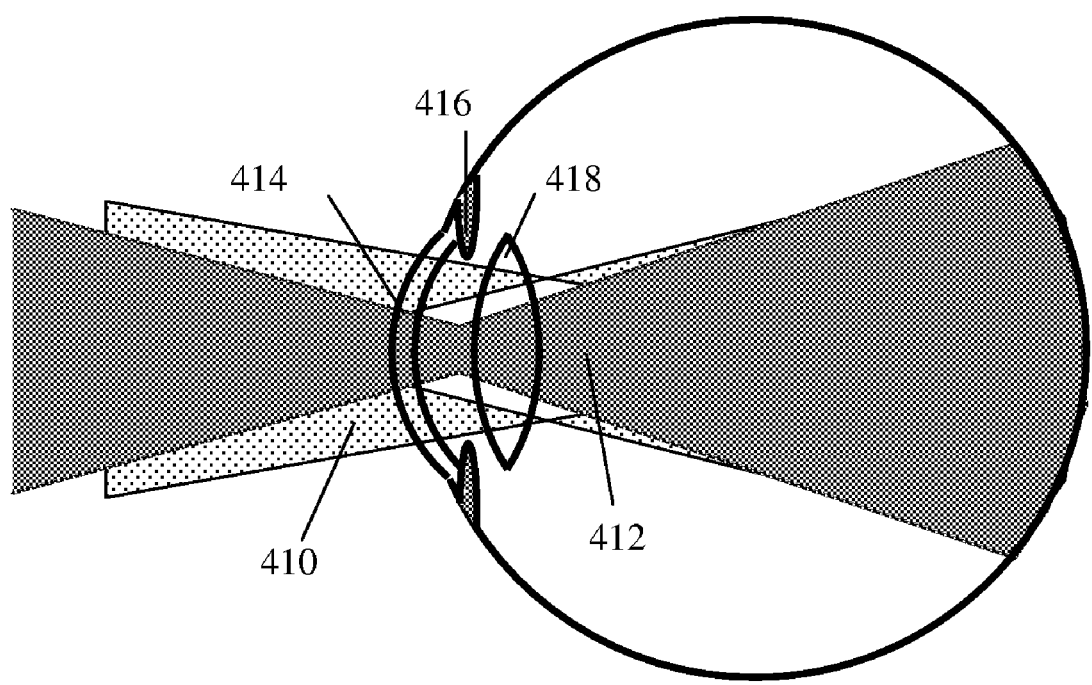
FIG. 4(a) shows an example of the overlap of the illumination path with the imaging path at the cornea side of the eye when the working distance is shorter than the correct working distance. The illumination light scattered by the cornea can now be captured by the imaging path.
Figure 4B:
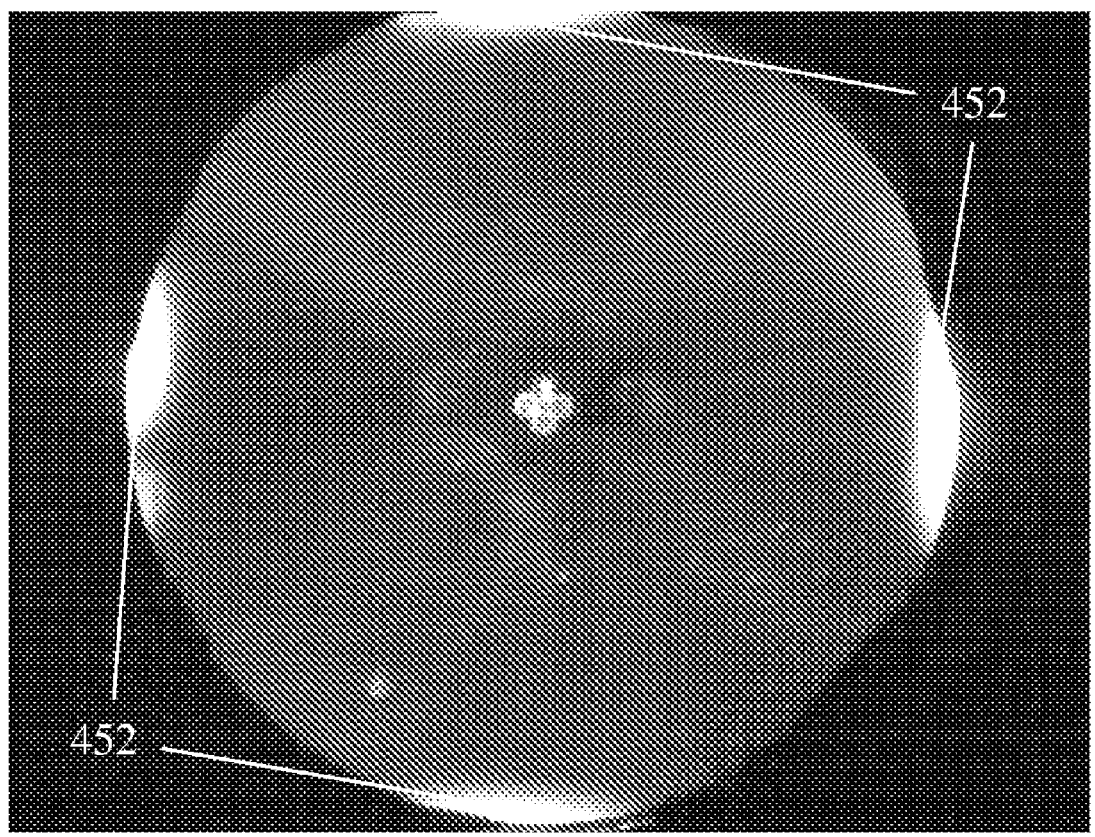
FIG. 4(b) shows an example of a typical near infrared retina image of an embodiment of the working distance sensor for the case of FIG. 4(a). Four relatively bright near infrared spots of scattered light from the cornea now appear at the horizontal and vertical edges of the working distance sensor viewing field.

Typically, if the working distance is shorter than the correct working distance as shown in FIG. 4(a), there will be an overlap of the illumination path 410 with the imaging path 412 at the cornea side 414 of the eye and as a result, as shown in FIG. 4(b), four relatively bright primary near infrared spots 452 of scattered light from the cornea would appear at the horizontal and vertical edges of the working distance sensor view field. The four bright spots will not be symmetric if the camera's horizontal and vertical alignment is not correct. Hence as one embodiment, the symmetry of the bright spots can be used to determine if the camera is transversely positioned correctly.

Figure 5A:
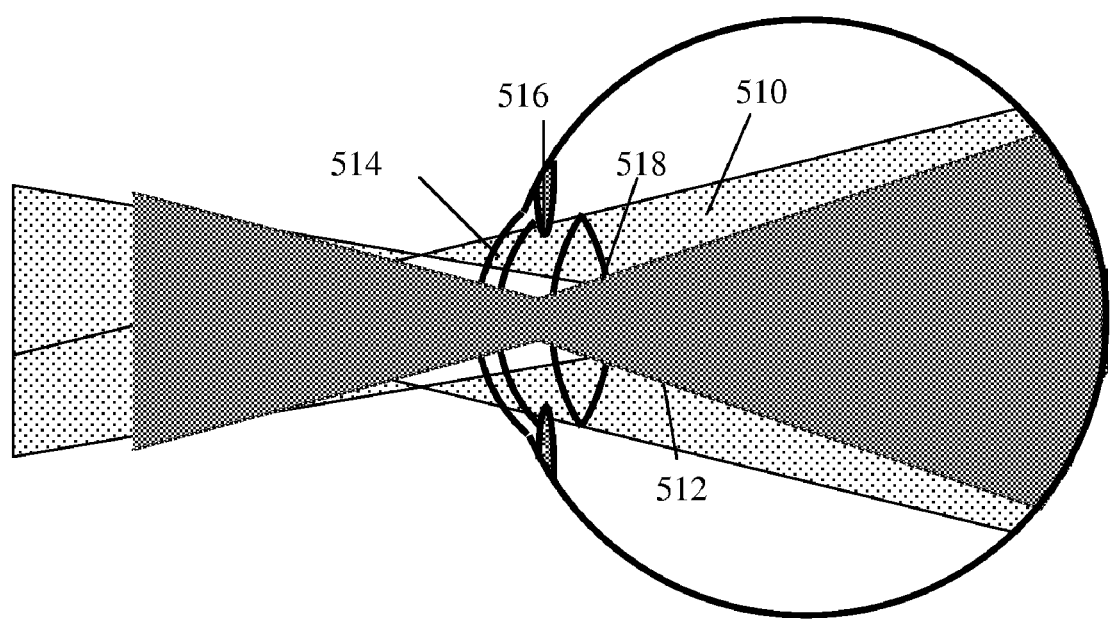
FIG. 5(a) shows an example of the overlap of the illumination path with the imaging path on the crystalline lens side of the eye when the working distance is longer than the correct working distance. The illumination light scattered by the crystalline lens can now be captured by the imaging path.

On the other hand, as shown in FIG. 5(a), if the camera body is pulled too far away from the eye such that the working distance is longer than the correct working distance, an overlap of the illumination path 510 with the imaging path 512 will occur at the crystalline lens region 518. Meanwhile, part of the illumination beam can be blocked and scattered by the iris 516, which will reduce the amount of illumination light onto the retina and make the illumination of the retina less efficient.

Figure 5B:
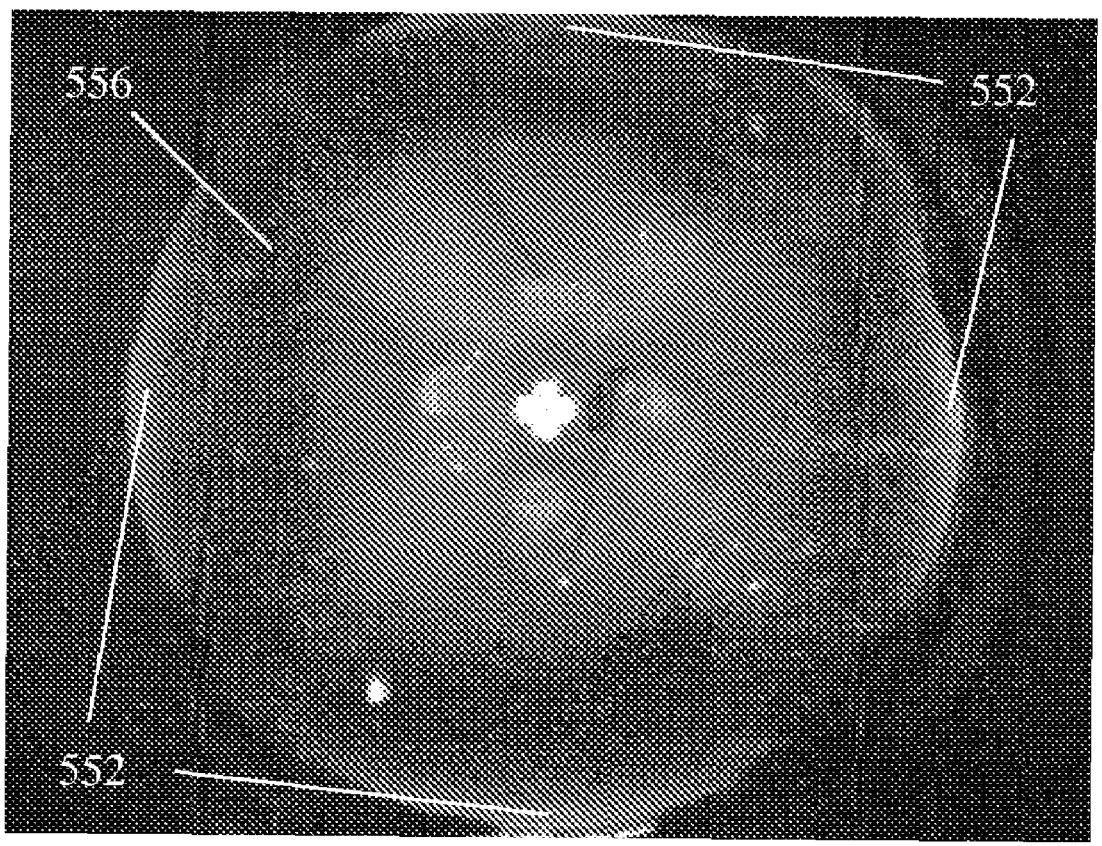
FIG. 5(b) shows a typical near infrared retina image of an embodiment of the working distance sensor for the case of FIG. 5(a). A dark band followed by four secondary diffused spots of weaker brightness now appear at the horizontal and vertical edges of the working distance sensor viewing field.

Generally, as shown in FIG. 5(b), a dark band 556 followed by four secondary diffused spots 552 of weaker brightness will appear at the horizontal and vertical edges on top of the live retina image. These four secondary weaker spots 552 are caused by the scattering of the four near infrared illumination beams from the crystalline lens.

Therefore, as one embodiment, a method to ensure a relatively good alignment of the fundus camera with respect to the eye is to initially adjust the camera to enable either the four primary brighter near infrared spots or the secondary weaker spots to firstly appear symmetrically at the four edges of the near infrared retina view, and then to axially move the camera until the four primary and/or secondary bright spots symmetrically disappear outwardly on the near infrared retina live image. This first method will enable the operator to position the fundus camera at substantially the correct position tolerance range. For many imaging cases, such as a 30° field of view non-stereo retina imaging, this first method will most likely be sufficient to ensure a flair-free color retina image.

However, for other more demanding retina imaging operation modes, such as fast sequential stereo 30° and especially 45° field of view retina imaging (see for example, U.S. Pat. No. 6,361,167), the range as determined by the above-mentioned approach may not be narrow enough to ensure a flair-free color retina image. This can happen because the near infrared image path can be slightly different from the visible retina image path, firstly as a result of the difference in the wavelength of the visible light and the near infrared light, and secondly as a result of the difference in the arrangement of the non-shared optical elements between the visible and near infrared retina imaging path. In addition, in obtaining a fast sequential stereo pair of fundus images, at least one optical element along the imaging path needs to be moved to create the left and right pair of the stereo retina images and hence the imaging path for the left and right retina images is in fact different from the mono or non-stereo retina imaging path used to produce the live near infrared retina image.

In another embodiment, various image pattern recognition algorithms can be applied to the live near infrared retina image to provide additional indications for more precise positioning so that a flair/haze-free color retina image can be obtained with a substantially increased success rate. In one example embodiment, a normalized gradient defined as $(I1-I2)/(I1+I2)$, where $I1$ and $I2$ are the averaged gray scales of two selected areas on the live near infrared view field, is employed to deduce a parameter in real time that can directly tell the operator with increased sensitivity if he or she has moved the camera to the correct position for optimum color retina imaging.

Figure 6:
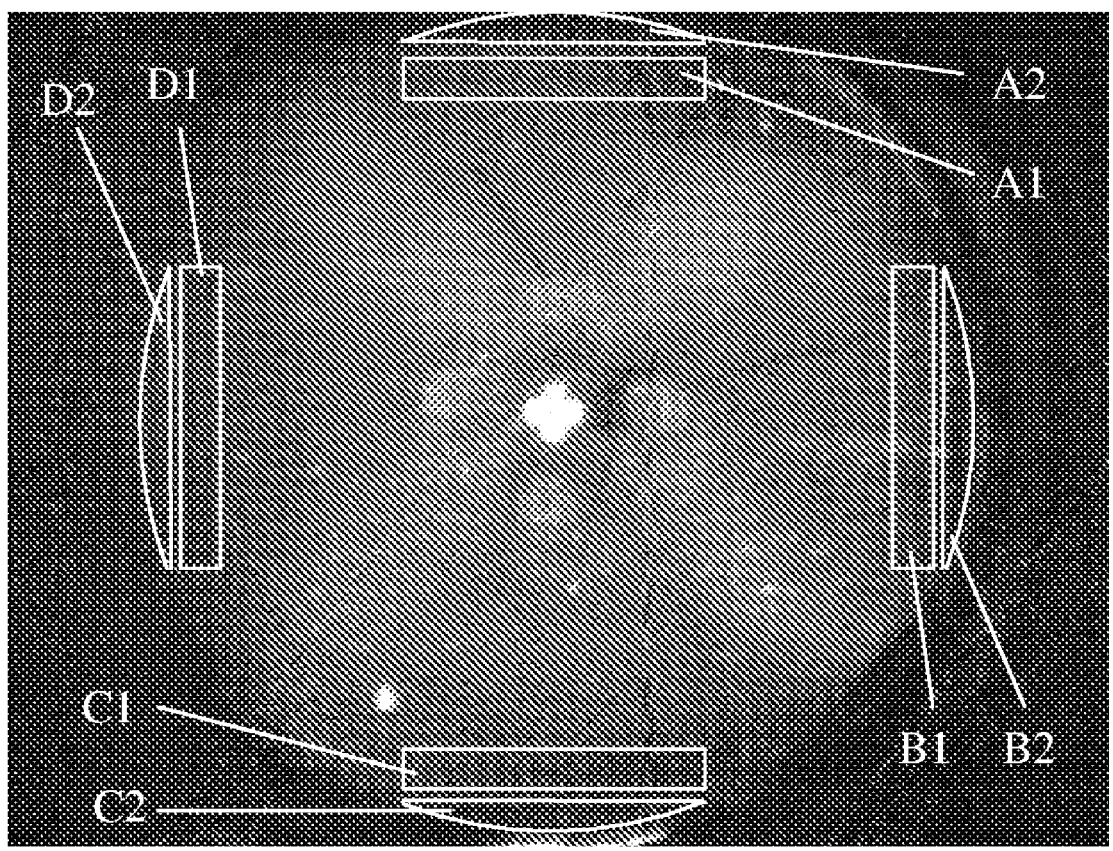
FIG. 6 shows an example of a pattern recognition algorithm that can be used to deduce a parameter to help the operator to position the fundus camera with improved accuracy. Four pairs of designated areas are drawn at the horizontal and vertical edges. Across each pair, a normalized gradient of averaged gray scale can be defined and summed to provide the parameter.

For example, if it happens that when the fundus camera is at the correct position, the dark band just starts to appear at the four peripheral edges of the near infrared live retina image, as shown in FIG. 6, four pairs of interested areas A1, A2, B1, B2, C1, C2 and D1, D2 near the horizontal and vertical edges of the live retina image can be selected. Regions A1, B1, C1 and D1 are designated so that when the fundus camera is well positioned both transversely and axially, the regions will overlap with the inner relatively uniform region of moderate brightness. Similarly, regions A2, B2, C2, D2 are designated so that when the fundus camera is well positioned both transversely and axially, the regions will overlap with the dark band as it just appears. The normalized gradient for each pair, $(IA1-IA2)/(IA1+IA2)$, $(IB1-IB2)/(IB1+IB2)$, $(IC1-IC2)/(IC1+IC2)$, and $(ID1-ID2)/(ID1+ID2)$, can be calculated and then summed in real time to provide a parameter Q as given below.

$$Q=(IA1-IA2)/(IA1+IA2)+(IB1-IB2)/(IB1+IB2)+(IC1-IC2)/(IC1+IC2)+(ID1-ID2)/(ID1+ID2)$$

It can now be seen that, when the fundus camera is correctly positioned, each pair of the designated regions will produce a maximum value of the normalized gradient and hence the summed parameter Q will also be a maximum. On the other hand, if the camera is only axially positioned away from the correct position, either the uniform moderate bright region will move outward to make the paired regions all moderately bright or the dark band will move inward to make the paired regions both relatively dark. In either case, the value of the Q parameter will drop.

Likewise, if the working distance is correct but the fundus camera is transversely positioned slightly off from the correct location, the dark band will move inward from one side and the opposing side of moderate uniform brightness region will move outside the view field. This will also cause the Q parameter to drop. In an extreme case of transversal or axial offset, a whole primary or secondary bright spot may get into the viewing field and this will tell the operator that the fundus camera is already off alignment.

Hence image pattern recognition can provide a more sensitive second method with improved precision in terms of positioning the fundus camera at the correct location with respect to the eye. A good practice would be to use the first method to achieve a first order position accuracy and then use the second method to achieve a better positioning accuracy.

Note that in the description of the above embodiments, four near infrared LEDs or fibers have been used as the light sources of the working distance sensor and the light sources are symmetrically position horizontally and vertically. However, this description is provided by way of example, not limitation, and different numbers of near infrared light sources can be used and the positions of these light sources can be varied with respect to the light illumination path. For example, the number of near infrared LEDs used can be eight and they can be positioned horizontally and vertically as well as diagonally. In addition, the near infrared light source can be directly tapped through some spectral filtering and optical fiber based light guiding from the Xenon arc lamp that provides the visible light source as a Xenon arc lamp also contains near infrared radiations.

In the above, embodiments have been described in which the near infrared illumination beams are spatially filtered and relayed optically in substantially the same way as the visible illumination beam, and the imaging path for the near infrared light is made substantially the same as for the visible light. However, there are alternative ways that the near infrared and visible illumination as well as imaging paths can be designed and arranged.

Figure 7:
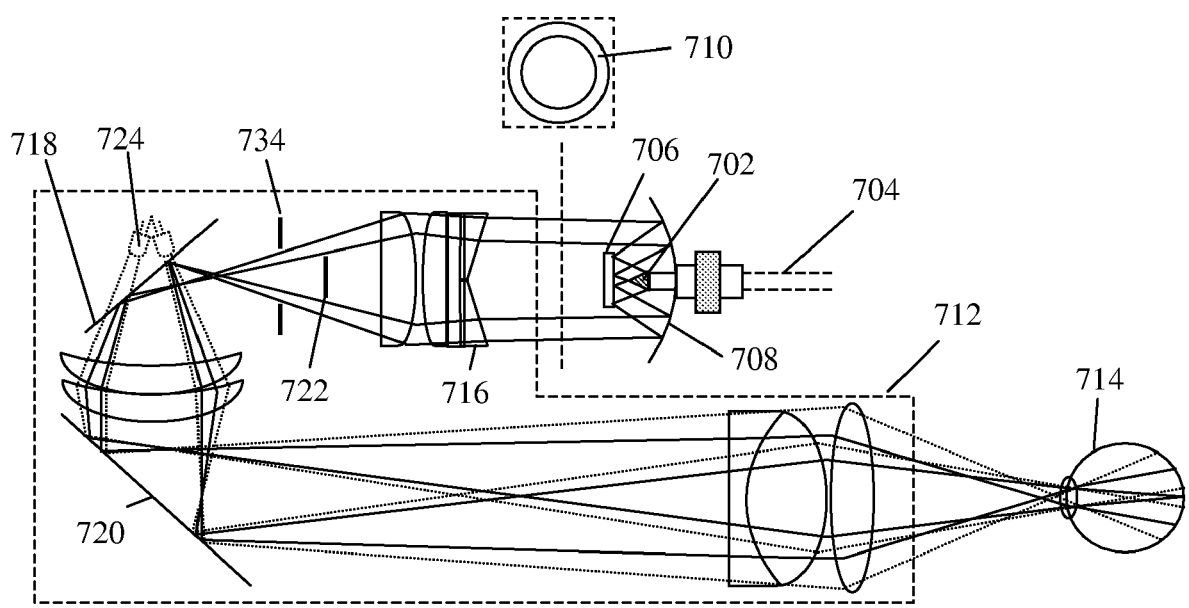
FIG. 7 shows an example of an alternative way to introduce the near infrared illumination beam into the illumination path. Near infrared LEDs are positioned behind a dichroic mirror that reflects visible light and transmits near infrared light.

For example, in another embodiment, as shown in FIG. 7, the near infrared LEDs can be positioned to project the near infrared beams into the illumination path after instead of before the effective annular ring spatial filters. In this embodiment, for example, a dichroic mirror 718 can be used that will reflect visible light and transmit near infrared light so that the near infrared LEDs can be properly positioned behind this dichroic mirror. In previous embodiments, the near infrared LEDs share the same space as the visible illumination light, and appear to locate on the visible annular ring. In this embodiment, the near infrared illumination light sources can be located closer or farther away from the optical axis, and to be made to reside inside or outside the visible annular ring, as shown by the dotted light rays in FIG. 7 along the illumination path.

As a result, the near infrared illumination beams, when relayed to the cornea region, will lie slightly inside and/or outside of the visible illumination beam. This arrangement creates different, but controllable, working distances for the visible and near infrared light.

This repositioning of the near infrared beams initially appears not to be ideal in terms of judging if there will be any flair or other artifact in the to-be-captured color retina image, but as long as the primary spots are not so bright to saturate the near infrared CCD camera and hence reduce the visibility of the optical disk and the major blood vessels on the retina, the primary spots can be used to improve the accuracy of fundus camera positioning.

For example, with the four bright primary spots located slightly closer to center in the live near infrared retina image, line patterns can be drawn designating regions on the live image screen such that when there is a match of the borders of the four primary spots with the designated regions, the fundus camera is at the correct (best designed) position. Therefore, the need to search in the dark is eliminated because the existence of the four bright primary spots at the edges within the live near infrared image indicate whether the fundus camera is positioned correctly. Meanwhile, if the working distance needs to be increased for another imaging condition, for example sequential stereo imaging, the camera can be pulled away further from the patient until the primary spots move to a second designated region or even until all disappear from the viewing field. As a result, one optical arrangement could provide two or more different indications for two or more different imaging conditions.

Alternatively, the same result of two or more indications for working distance can also be achieved by manipulating the imaging aperture of the near infrared imaging path, to make it reside either with the visible illumination path or partially away from the visible illumination path. The optical stop of the visible retina imaging path can be made different from (for example, smaller than) that of the near infrared imaging path. As the camera is at the correct working distance, the cornea scattered bright spots would appear near the edge of the near infrared monitor, even though the artifact would not appear in the visible image. This design will also get rid of the "search in the dark" problem. Similar to the previous embodiment, the primary spots would disappear when the camera is moved to another position for the second indication. When image recognition algorithms are applied to an image with patterns having a higher contrast, the algorithm can also produce a substantially improved sensitivity in the determination of the best fundus camera position. A similar effect can also be achieved by deliberately making the near infrared image path different from the visible imaging path.

Figure 8:
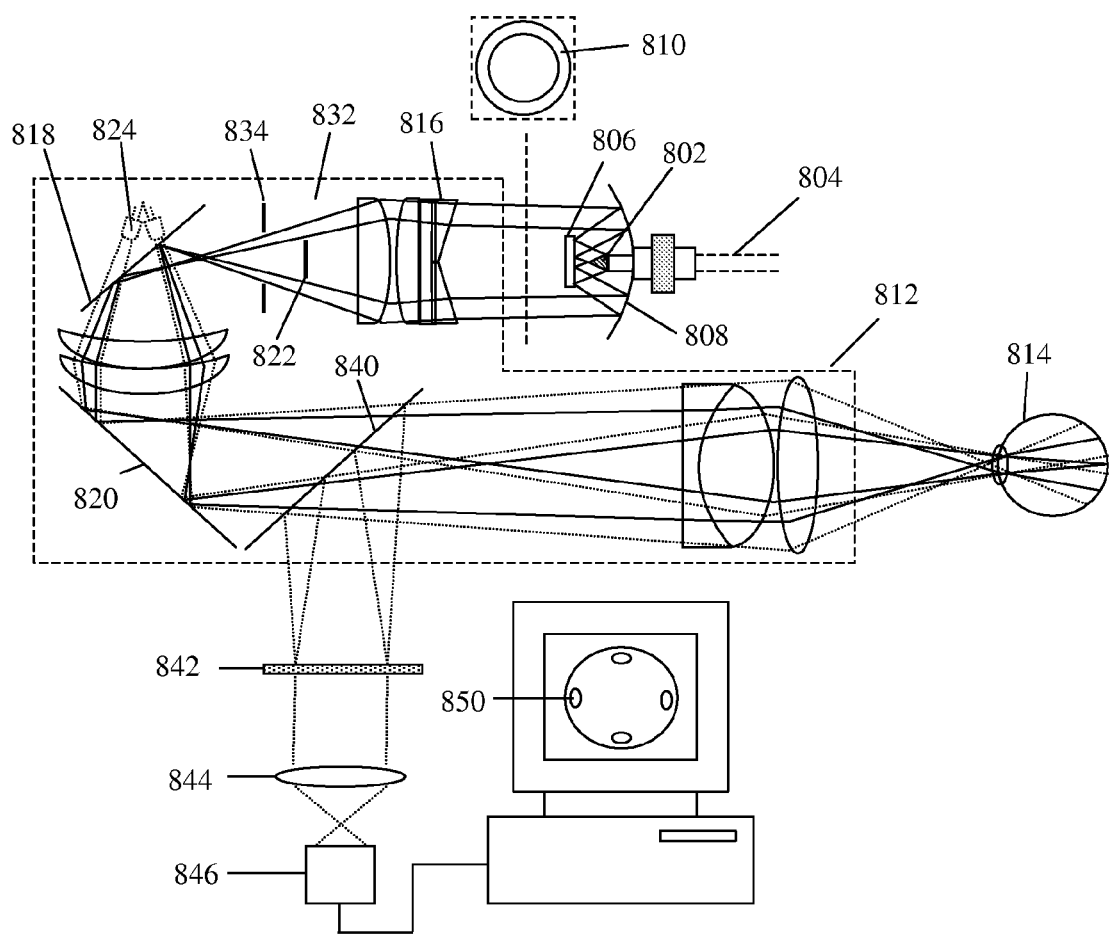
FIG. 8 shows an alternative embodiment of the working distance sensor in which a small fraction of the cornea scattered near infrared light spots are directed and imaged onto a ground glass plate and the image is captured by a CCD.

In another embodiment as shown in FIG. 8, a partial beam splitter 840 can be arranged in the optical path to direct a small fraction of the returned near infrared light to a ground glass plate 842 that is placed at a conjugate plane of the cornea such that cornea scattered bright near infrared light spots are projected onto the ground glass plate 842. A near infrared CCD 846 can be combined with a lens 844 to capture the image of the cornea scattered near infrared bright spots and to display the bright spots 850 on a monitor. Real time pattern recognition algorithms as described above can again be used to indicate if the imaged bright spots are at the desired location and hence to indicate if the camera is correctly positioned. In doing so, the near infrared light sources can also be arranged to lie inside or outside the visible illumination path, adding more flexibility to the design. In this design, the near infrared CCD is used to function purely as a working distance sensor to provide the real time data for the image pattern recognition algorithm. It is therefore possible to hide the distance sensor image and just to show the processed positioning information obtained from the algorithm and display it on the monitor of the live near infrared retina image.

Figure 9:
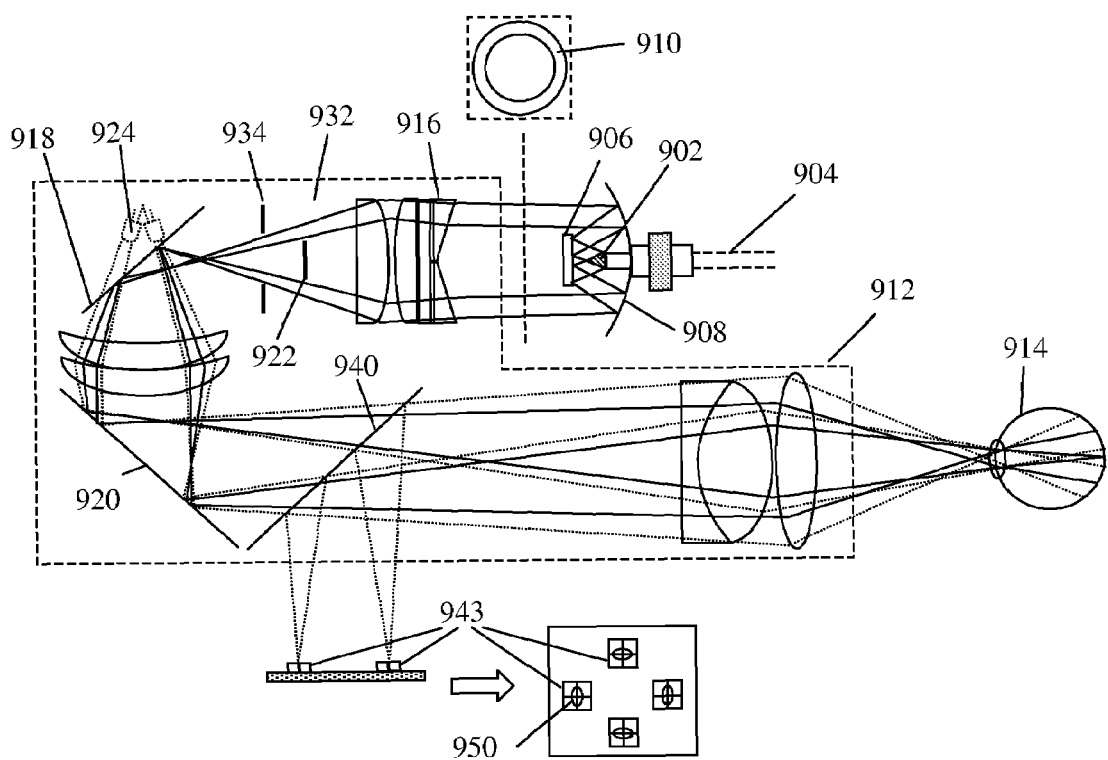
FIG. 9 shows another embodiment of the working distance sensor in which a number of light spot position sensors are used to sense the image position of the cornea scattered near infrared light spots and to indicate if the camera is positioned correctly or not.

In still another embodiment as shown in FIG. 9, the ground plate can be replaced with a number of light spot position sensors such as quadrant detectors 943. These position sensors can be adjusted such that when the camera is at the correct position, the cornea scattered bright spots 950 are at the center of each position sensor. As a result, the readout from the light spot position sensors can be used to indicate if the camera is positioned correctly or not and this information can also be displayed on the monitor of the live near infrared retina image.

In still another embodiment, an independent alignment sensor can be added to display a live near infrared image of the anterior segment of the patient's eye. Since near infrared light is used, this alignment sensor should be able to provide a live image of the iris of the eye without causing the iris to constrict. The operator can use this alignment sensor to initially do a coarse alignment of the fundus camera with the center of the patient's iris before switching to the working distance sensor for a refined positioning of the fundus camera. The operator can also use this alignment sensor to measure the dilation level of the iris and use these measurements to judge whether the dilation is sufficient for mono or stereo imaging.

Figure 10:
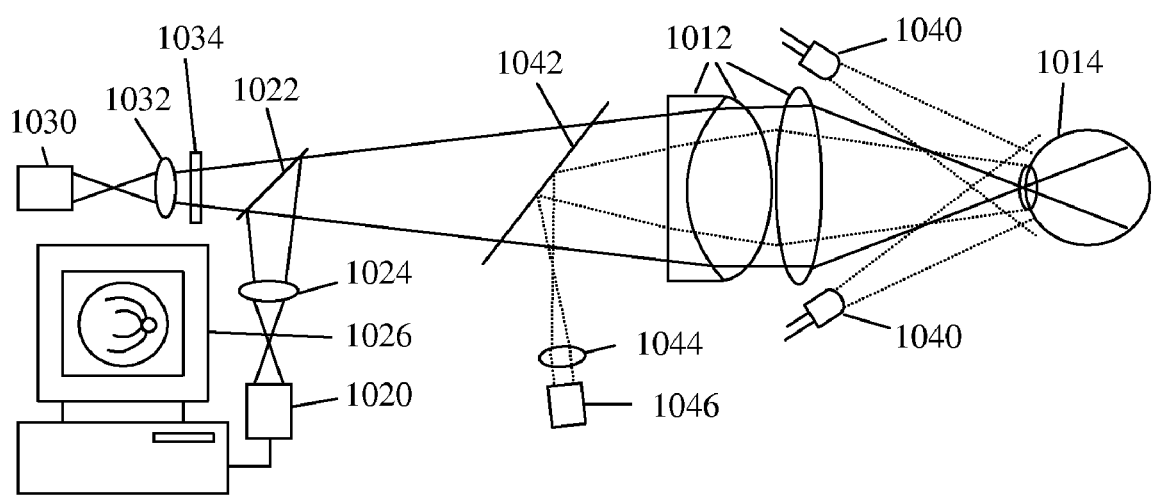
FIG. 10 shows an example of an arrangement of an added alignment sensor to the working distance sensor to display a live near infrared image of the anterior segment of the patient's eye.

As shown in FIG. 10, in this embodiment an independent alignment sensor is constructed by attaching a number of near infrared light sources 1040 (for example, two LEDs with a center wavelength of 760 nm) outside the peripheral of the objective lens 1012. The LEDs are selected to have a desired divergent angle and illumination uniformity so that the illuminated area on the anterior of the eye 1014 at the correct working distance is large enough to fully cover the area of interest and also enable a good contrast of the near infrared iris image. A near infrared beam splitter 1042 is mounted behind the objective lens 1012 to divert a small portion of light from the main optical path to another near infrared CCD 1046 to form an image of the anterior of the eye.

The beam splitter 1042 can be made of a very thin glass plate (for example, 400 micron in thickness), and can be coated with a broadband antireflection coating such that only a very small fraction of light (for example, less than 1% for a wavelength range from 450 nm to 850 nm on average for both polarizations) will be reflected. Such a coating reduces the light loss for the visible imaging light and the working distance sensor imaging light, both of which pass through the beam splitter 1042.

A group of optical lenses 1044 can be placed between the thin glass plate beam splitter 1042 and the near infrared CCD camera 1046 (the alignment sensor). Together with the objective lens(es) 1012 for retina imaging, this lens group 1044 relays the image of the patient's iris to the alignment sensor CCD 1046. The aperture of this image relay system can be selected to control the depth of focus so that both the iris and the corneal area are within focus. On the other hand, the depth of focus is preferably limited to a degree such that the near infrared image is only in focus when the patient's eye is located near the correct working distance.

To reduce the cross talk of scattered light from the working distance sensor to the alignment sensor, a bandpass optical filter (for example, with a center wavelength of 760 nm and a FWHM (full width half maximum) of 65 nm) can be placed in front of the alignment sensor near infrared CCD 1046. The filter should block most of the light with wavelengths shorter than 720 nm and longer than 800 nm.

The two 760 nm LEDs 1040 can be controlled to produce radiation at a level that does not cause dilation of the iris and light saturation on the alignment sensor CCD 1046. In this example, the iris alignment image can be displayed on the same or a different screen from that for the working distance sensor image.

Figure 11:
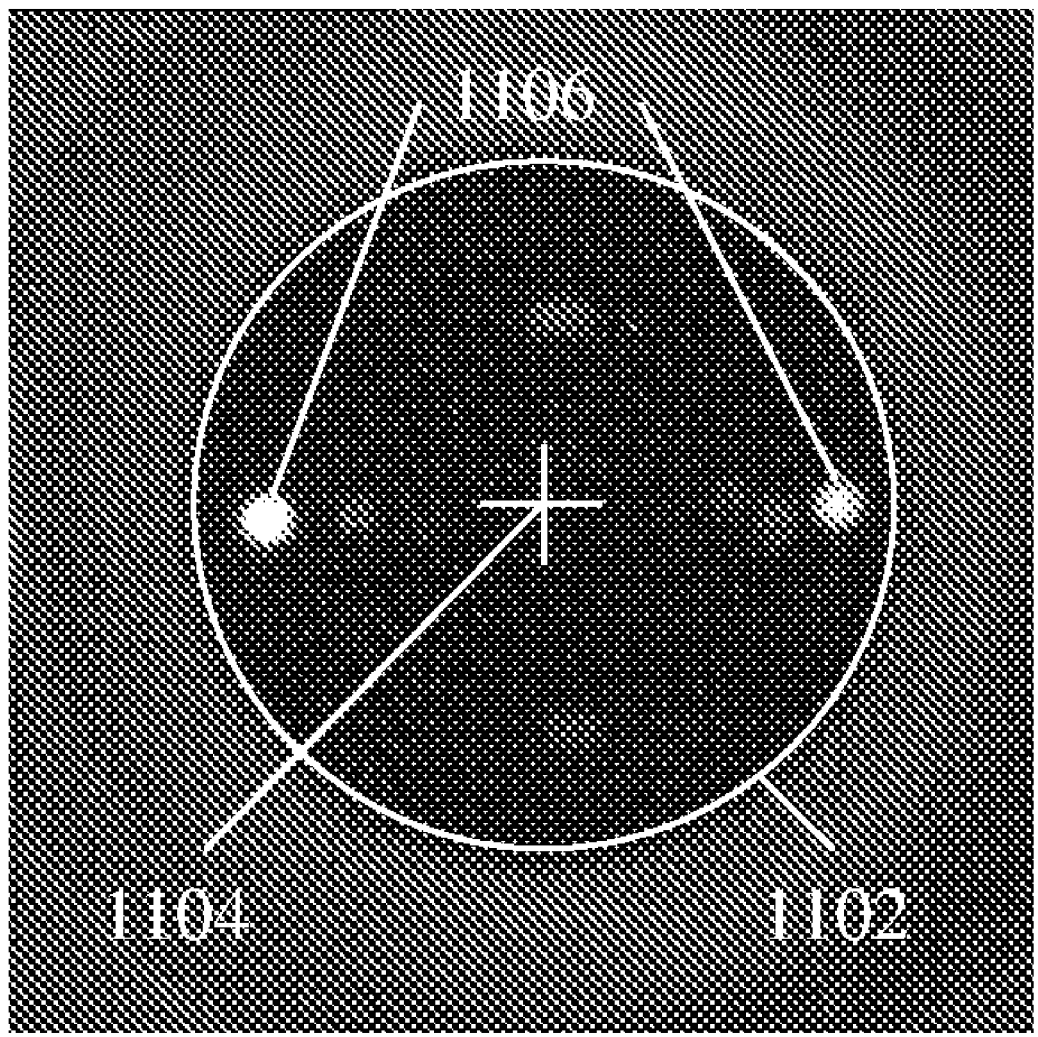
FIG. 11 shows an example of an image produced by the alignment sensor embodiment of FIG. 10. A circle and/or a cross can be drawn to assist the operator in doing a coarse iris alignment as well as in judging if the iris is opened enough for a certain mode of fundus imaging (such as mono or stereo at 30° or 45°).

As shown in FIG. 11, a circle 1102 and/or a cross 1104 can be drawn on the alignment sensor screen so that when the iris of the patient's eye is co-centered with the drawn circle 1102 or centered at the drawn cross 1104 and is focused with the iris appearing clear in the image, the coarse iris alignment is considered good enough. The circle 1102 can also serve the purpose of allowing the operator to check the dilation level of the iris and to use these measurements to judge whether the dilation is sufficient for different modes of imaging such as stereo imaging at 30° or 45° field of view. The size of the circle 1102 can also be automatically changed and displayed for different field of view angles (for example, 30° and 45° field of view) and for different modes of operation of the fundus camera (for example, mono and stereo).

Alternatively, multiple circles can be displayed simultaneously on the monitor screen to cater for different modes of operation of the camera. The alignment sensor can also be arranged such that the reflection or scattering of the two 760 nm LEDs from the cornea is also captured by the alignment sensor to produce two near infrared bright spots 1106 and these two bright spots 1106 can be made to be well focused on the alignment sensor image when the eye is positioned close to the correct working distance, which will help the operator to also achieve a coarse axial alignment using this alignment sensor.

Note that in addition to the use of a different wavelength range to reduce the crosstalk between the alignment sensor and the working distance sensor, temporal separation techniques can also be used to turn the light sources on and off sequentially to achieve the same goal.

It should be understood that in addition to fundus cameras, the features disclosed here can also be applied to other optical medical imaging devices such as ophthalmoscopes, microscopes and endoscopes. The concept of combining two spectral ranges of illumination light for live samples that may respond to one spectral range of illumination light can be extended to any case in which the other spectral range illumination light can be initially used to provide a live image of the object without affecting the imaging condition of the overall optical system as a result of light stimulation to a live sample before the other spectral range illumination light is turned on to get an image of the sample.

The invention has now been described with reference to the preferred embodiments. Alternatives and substitutions will now be apparent to persons of skill in the art. Accordingly, it is not intended to limit the invention except as provided by the appended claims.

What is claimed is:

1. A method comprising:
   projecting light from a near infrared light source into an annular visible light illumination path of a fundus camera to form a near infrared illumination beam;
   spatially filtering the near infrared illumination beam to form an annular near infrared illumination beam substantially overlapping the annular visible light illumination path, with the annular visible light illumination path configured so that visible light projected into the annular visible light illumination path forms an annular visible light illumination beam that illuminates the retina of an eye of a subject;
   focusing the annular near infrared illumination beam and the annular visible light illumination beam to an annular ring at the cornea region of the eye of a subject; and
   tapping a portion of a near infrared imaging beam, formed when the annular near infrared illumination beam is reflected from the cornea and/or retina of the eye of a subject, to form a tapped portion directed to a sensor that forms a near infrared image of the cornea and/or retina of the eye, and where the annular near infrared illumination beam and the near infrared imaging beam do not overlap at the cornea region when a working distance value between an objective lens and the anterior surface of the eye is correct so that only an image of the retina is formed at the sensor.

2. The method of claim 1 further comprising:
analyzing a near infrared image of the retina of the eye formed by the sensor from the tapped portion of the near infrared imaging beam; and
adjusting a working distance value between an objective lens and the eye based on results of analyzing the near infrared image of the retina.

3. The method of claim 2 further comprising:
increasing the working distance value if flare due to reflection from the cornea of the eye is visible in the near infrared image of the retina formed by the sensor.

4. The method of claim 2 further comprising:
decreasing the working distance value if a dark band is visible in the near infrared image of the retina formed by the sensor.

5. The method of claim 2 where the objective lens is part of a fundus camera and further comprising:
measuring the normalized gradient values of the intensity of a plurality of designated areas of a near infrared image of the retina formed by the sensor; and
adjusting the working distance value and/or the transverse position of the fundus camera until a sum of the normalized gradient values is substantially equal to a maximum value.

6. A system comprising:
means for projecting light from a near infrared light source into an annular visible light illumination path of a fundus camera to form a near infrared illumination beam;
means for spatially filtering the near infrared illumination beam to form an annular near infrared illumination beam substantially overlapping the annular visible light illumination path, with the annular visible light illumination path configured so that visible light projected into the annular visible light illumination path forms an annular visible light illumination beam that illuminates the retina of an eye of a subject;
means for focusing the annular near infrared illumination beam and the annular visible light illumination beam to an annular ring at the cornea region of the eye of a subject; and
means for tapping a portion of a near infrared imaging beam, formed when the annular near infrared illumination beam is reflected from the cornea and/or the retina of the eye of the subject to form a tapped portion directed to a sensor that forms a near infrared image of the cornea and/or retina of the eye, and where the annular near infrared illumination beam and the near infrared imaging beam do not overlap at the cornea region when a working distance value between an objective lens and the anterior surface of the eve is correct so that only an image of the retina is formed at the sensor.

7. The system of claim 6 further comprising:
means for analyzing a near infrared image of the retina formed by the sensor from the tapped portion of the near infrared imaging beam to adjust a working distance value between an objective lens and the eye.

8. The system of claim 7 further comprising:
means for increasing the working distance value if flare due to reflection from the cornea of the eye is visible in the near infrared image of the retina formed by the sensor.

9. The system of claim 7 further comprising:
means for decreasing the working distance value if a dark band is visible in the near infrared image of the retina formed by the sensor.

10. The system of claim 7 where the objective lens is part of a fundus camera and further comprising:
means for measuring the normalized gradient values of the intensities of a plurality of designated areas of the near infrared image of the retina formed by the sensor; and
means for adjusting the working distance value and/or the transverse position of the fundus camera until a sum of the normalized gradient values is substantially equal to a maximum value.

11. A system comprising:
a plurality of near infrared light sources;
a mounting structure for holding said light sources;
a projecting optical element adapted to project near infrared light from the light sources into an annular ring-shaped visible light illumination path of a fundus camera to form a plurality of near infrared illumination beams, with the annular ring-shaped visible light illumination path configured so that visible light projected into the annular ring-shaped visible light illumination path forms an annular ring-shaped visible light illumination beam that illuminates the retina of the eye of a subject;
an aperture structure for spatially filtering the near infrared illumination beams to cause the near infrared illumination beams to substantially overlap the annular ring-shaped visible light illumination path;
an optical relay system configured to focus the annular ring-shaped visible light illumination beam to a focused visible light annular ring at the cornea of the eye of a subject and to focus the near infrared illumination beams to a plurality of focused infrared light spots around an annular ring that substantially overlaps the focused visible light annular ring at the cornea region of the eye of a subject;
an optical element that taps a portion of a near infrared imaging beam, formed when the plurality of the near infrared illumination beams are reflected from the cornea and/or retina of the eye; and
a sensor, positioned to receive a tapped portion of the near infrared illumination beam, that forms a near infrared image of the of the cornea and/or retina and where the near infrared illumination beam and the near infrared imaging beam do not overlap at the cornea when a working distance value between an objective lens and the anterior surface of the eye is correct so that only an image of the retina is formed at the sensor.

12. The system of claim 11 further comprising:
an image processing element that processes said near infrared image to determine a working distance value of the eye from an objective lens.

13. The system of claim 12 with said image processing element being configured to measure the normalized gradient values of intensity at designated image regions of the image and to indicate a correct working distance value when the sum of the normalized gradient values is substantially equal to a maximum value.

14. The system of claim 11 where the projecting optical element is a dichroic mirror.

15. The system of claim 11 where the mounting structure is a ring.

16. The system of claim 11 where the aperture structure includes an obscuration disk.

17. A method comprising:
projecting light from a plurality of near infrared light sources into an annular ring-shaped visible light illumination path of a fundus camera to form a plurality of near infrared illumination beams, with the annular ring-shaped visible light illumination path configured so that visible light projected into the annular ring-shaped visible light illumination path forms an annular ring-shaped visible light illumination beam that illuminates the retina of the eye of a subject;
controlling the path of the near infrared illumination beams to be slightly inside and/or slightly outside of the annular ring-shaped visible light illumination path;
focusing the annular ring-shaped visible light illumination beam to a focused visible light annular ring at the cornea of the eye of the subject;
focusing the plurality of near infrared illumination beams to a corresponding number of focused light spots around an annular ring that resides slightly inside and/or outside the focused visible light annular ring at the cornea region of the eye of a subject; and
tapping a portion of a near infrared imaging beam reflected from the cornea and/or retina of the eye of a subject to direct the tapped portion to a sensor that forms a near infrared image of the retina.

18. The method of claim 17 further comprising:
analyzing the near infrared image; and
adjusting the working distance between an objective lens and the eye.

19. The method of claim 18 where the step of analyzing further comprises:
determining the location of reflected images of the near infrared light beams scattered from the cornea to measure a working distance.

20. The method of claim 18 where the step of adjusting further comprises:
varying the distance between the eye and objective lens based on the location of the reflected images of the near infrared light beams scattered from the cornea.

21. A system comprising:
means for projecting light from a plurality of near infrared light sources into an annular ring-shaped visible light illumination path of a fundus camera to form a plurality of near infrared illumination beams, with the annular ring-shaped visible illumination light path configured so that visible light projected into the annular ring-shaped visible light illumination path forms an annular ring-shaped visible light illumination beam that illuminates the retina of the eye of a subject;
means for controlling the path of the near infrared illumination beams to be slightly inside and/or slightly outside of the annular ring-shaped visible light illumination path;
means for focusing the annular ring-shaped visible light illumination beam to a focused visible light annular ring at the cornea of the eye of the subject;
means for focusing the plurality of near infrared illumination beams to a corresponding number of focused light spots around an annular ring that resides slightly inside and/or outside the focused visible light annular ring at the cornea region of the eye of a subject; and
means for tapping a portion of a near infrared imaging beam reflected from the cornea and/or retina of the eye of a subject to direct the tapped portion to a sensor that forms a near infrared image of the retina.

22. The system of claim 21 further comprising:
means for analyzing the near infrared image; and
means for adjusting the working distance between an objective lens and the eye.

23. The system of claim 22 where the step of analyzing further comprises:
means for determining the location of reflected images of the near infrared beams scattered from the cornea to measure a working distance.

24. The system of claim 22 where the step of adjusting further comprises:
means for varying the distance between the eye and objective lens based on the location of the reflected images of the near infrared light beams scattered from the cornea.

25. A system comprising:
a plurality of near infrared light sources;
a mounting structure for holding said light sources;
a projecting optical element adapted to project near infrared light from the light sources into an annular ring-shaped visible light illumination path of a fundus camera to form a plurality of near infrared illumination beams with the near infrared illumination beams being disposed slightly inside and/or outside of the annular ring-shaped visible light illumination path, with the annular ring-shaped visible light illumination path configured so that visible light projected into the annular ring-shaped visible light illumination path forms an annular ring-shaped visible light illumination beam that illuminates the retina of the eye of a subject;
an optical relay system configured to focus the annular ring-shaped visible light illumination beam to a focused visible light annular ring at the cornea of the eye of the subject and to focus the plurality of near infrared illumination beams to a corresponding number of focused light spots around an annular ring that resides slightly inside and/or outside the focused visible light annular ring at the cornea region of the eye of a subject;
an optical element that taps a portion of a near infrared imaging beam reflected from cornea and/or retina of the eye; and
a sensor, positioned to receive a tapped portion, that forms a near infrared image of the retina.

26. The system of claim 25 further comprising:
an image processing element that processes said image to determine the working distance of the eye from an objective lens.

27. The system of claim 26 with said image processing element being configured to measure the location of reflected images of the near infrared light beams scattered from the cornea to measure a working distance.

28. The system of claim 25 where the projecting optical element is a dichroic mirror.

29. The system of claim 25 where the mounting structure is a ring.

30. A system comprising:
a first plurality of infrared light sources;
a mounting structure for holding said light sources in said plurality;
a projecting optical element adapted to project infrared light from the light sources in the first plurality into an annular ring-shaped visible light illumination path of a fundus camera to form a plurality of first infrared illumination beams with the annular ring-shaped visible light illumination path configured so that visible light projected into the annular ring-shaped visible light illumination path forms an annular ring-shaped visible light illumination beam that illuminates the retina of the eye of a subject;

an aperture structure for spatially filtering the plurality of first infrared illumination beams to cause the near infrared illumination beams to substantially overlap the annular ring-shaped visible light illumination path;

a first optical relay system configured to focus the annular ring-shaped visible light illumination beam to a focused visible light annular ring at the cornea region of the eye of the subject and to focus the near infrared illumination beams to a number of focused light spots around an annular ring that substantially overlaps with the focused visible annular ring at the cornea region of the eye;

a first optical element that taps a portion of the plurality of first infrared illumination beams reflected from the cornea and/or retina of the eye of a subject to form a first infrared imaging beam where the plurality of first infrared illumination beams and the first infrared imaging beam do not overlap at the cornea when a working distance value between an objective lens and the anterior surface of the eye is correct so that only an image of the retina is formed at a sensor;

a second plurality of near infrared light sources aligned to illuminate the iris of the eye and form a second near infrared imaging beam reflected from the iris; and a second optical element for tapping a portion of the second near infrared imaging beam reflected from the iris of the eye.

31. The system of claim 30 further comprising:
a first sensor, positioned to receive a tapped portion of the first near infrared imaging beam, to form an image of the retina; and
a second sensor, positioned to receive a tapped portion of the second near infrared imaging beam, to form an image of iris.

32. The system of claim 30 further comprising:
a display, having a screen, for displaying the image of the iris on the screen, with the display having a circle drawn on the screen positioned to indicate the dilation of an iris having an image displayed on the screen.

33. The system of claim 30 where the light sources of the first and second plurality have different wavelengths and further comprising:
a bandpass filter for selectively passing only light from the second plurality of infrared light sources to eliminate crosstalk.

34. A method comprising:
projecting light from a plurality of infrared sources onto the iris of an eye;
capturing a part of the infrared light reflected from the iris and directing captured light to a sensor that forms an infrared image of the iris;
displaying the image of the iris on a screen;
comparing the image of the iris to a circle drawn on the screen to determine the dilation of the iris; and
automatically changing the size of the circle drawn according to the field of view and/or mode of operation of a fundus camera.

* * * * *